United States Patent
Mohammadi et al.

(10) Patent No.: US 8,357,360 B2
(45) Date of Patent: *Jan. 22, 2013

(54) COSMETIC COMPOSITIONS CONTAINING AN AQUEOUS DISPERSION OF SILICONE ELASTOMERS AND METHODS OF USE

(75) Inventors: Fatemeh Mohammadi, Hauppauge, NY (US); Czarnota Anna, Huntington, NY (US)

(73) Assignee: E-L Management Corp., New York, NY (US)

( * ) Notice: Subject to any disclaimer, the term of this patent is extended or adjusted under 35 U.S.C. 154(b) by 1355 days.

This patent is subject to a terminal disclaimer.

(21) Appl. No.: 11/112,525

(22) Filed: Apr. 23, 2005

(65) Prior Publication Data

US 2006/0239950 A1    Oct. 26, 2006

(51) Int. Cl.
*A61Q 19/08* (2006.01)
*A61K 8/02* (2006.01)
*A61K 8/04* (2006.01)
*A61K 8/92* (2006.01)
*A61K 8/97* (2006.01)
*A61K 8/98* (2006.01)

(52) U.S. Cl. .............. 424/78.03; 424/70.12; 424/74

(58) Field of Classification Search .............. None
See application file for complete search history.

(56) References Cited

U.S. PATENT DOCUMENTS

| | | | |
|---|---|---|---|
| 5,244,598 A | 9/1993 | Merrifield et al. | |
| 5,871,761 A | 2/1999 | Kuwata et al. | |
| 5,928,660 A | 7/1999 | Kobayashi et al. | |
| 6,262,170 B1 | 7/2001 | Kilgour et al. | |
| 6,346,583 B1 | 2/2002 | Kilgour et al. | |
| 6,350,460 B1 | 2/2002 | Andrews et al. | |
| 6,387,508 B1 | 5/2002 | Guilbert et al. | |
| 6,409,997 B1 | 6/2002 | Castro | |
| 6,770,708 B2 | 8/2004 | Kadlec et al. | |
| 2002/0106385 A1 * | 8/2002 | Vatter et al. | 424/401 |
| 2003/0007985 A1 | 1/2003 | Chevalier et al. | |
| 2003/0219395 A1 | 11/2003 | Sakuta | |
| 2004/0126349 A1 | 7/2004 | Anderson et al. | |
| 2004/0258721 A1 * | 12/2004 | Bauer et al. | 424/401 |
| 2005/0100568 A1 * | 5/2005 | De Mul et al. | 424/401 |
| 2005/0276761 A1 * | 12/2005 | Gupta | 424/59 |
| 2006/0013791 A1 * | 1/2006 | Shimizu et al. | 424/70.12 |

FOREIGN PATENT DOCUMENTS

| | | |
|---|---|---|
| EP | 0829253 | 3/1998 |
| EP | 1 136 064 | 9/2001 |
| JP | 11-217324 | 8/1999 |
| JP | 2001-048729 | 2/2001 |
| JP | 2004-210662 | 7/2004 |
| WO | WO 02/03950 | 1/2002 |
| WO | WO02/96571 | 5/2002 |
| WO | WO 02/092047 | * 11/2002 |
| WO | WO 03/028690 | * 4/2003 |
| WO | WO03/035016 | 5/2003 |
| WO | WO2004/100906 | 11/2004 |

OTHER PUBLICATIONS

PCT International Search Report; International Application No. PCT/US06/013958; Completion Date: Aug. 1, 2006; Date of Mailing: Aug. 1, 2006.
PCT Written Opinion of the International Searching Authority, or the Declaration; International Application No. PCT/US06/013958; Completion Date: Aug. 1, 2006; Mailing Date: Aug. 1, 2006.

* cited by examiner

*Primary Examiner* — Kevin S Orwig
(74) *Attorney, Agent, or Firm* — Peter Giancana

(57) ABSTRACT

An anti-aging composition comprising more than 30% by weight of an aqueously dispersed silicone elastomer and an emollient system and methods of use thereof for improving skin condition.

10 Claims, No Drawings

COSMETIC COMPOSITIONS CONTAINING AN AQUEOUS DISPERSION OF SILICONE ELASTOMERS AND METHODS OF USE

FIELD OF THE INVENTION

The present invention relates to skin care cosmetic compositions and methods. In particular, the present invention relates to novel cosmetic compositions containing an aqueous dispersion of silicone elastomers, and methods of use thereof.

BACKGROUND OF THE INVENTION

In an era that seeks to prolong youth in every possible way, quick remedies for diminishing the appearance of lines and wrinkles due to aging are highly sought. Products incorporate herbal extracts, vitamins, sunscreens and the like, claiming to improve the skin condition by providing anti-aging benefits. Quick remedies often include plastic surgery, Botox® injections and collagen injections. However, such remedies are often painful and too expensive for the average consumer. Therefore, there is still a need for cost-effective skin care products that can be topically applied to provide a quick reduction in the appearance of lines and wrinkles.

Silicone elastomers have been incorporated in skin care systems to create skin softening effects and are typically in silicone based compositions. However, water-based compositions are highly sought because of their moisturizing nature. Although silicone elastomers can be incorporated into the hydrophobic phase of an emulsion, the benefits can be diluted in such form. Moreover, some methods teach the dispersion of fine particles of silicone within a water phase to provide a skin smoothening effect. However, because of the low hydrophilicity of the silicone elastomer particles, uniform dispersability is difficult and therefore the benefits of such silicone particles are diminished. Moreover, the elastomers are only used in low amounts because the systems may become unstable when used in high concentrations. See U.S. Pat. No. 5,871,761. Therefore, the smoothening effects of the elastomers are proportionally limited. Further, since the silicone elastomers are hydrophobic, their skin softening effects may be diminished if not used with a suitable combination of ingredients in an aqueous medium.

Therefore, there still exists a need for an anti-aging product that provides a quick reduction in the appearance of lines and wrinkles.

SUMMARY OF THE INVENTION

The present invention provides an anti-aging composition comprising more than 30% by weight of an aqueously dispersed silicone elastomer and an emollient system.

The present invention provides further provides a method of improving skin condition and reducing the appearance of lines and wrinkles by applying to the skin a composition comprising more than 30% by weight of an aqueous dispersion of silicone elastomer and an emollient system.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

Certain aqueous dispersions of silicone elastomers have a softening effect when applied onto the skin. By the term softening, it is meant that the human skin feels smoother and softer to the touch after topical application of the aqueous dispersion of silicone elastomers. Such aqueous dispersions are suspended within an aqueous medium to provide skin care benefits in water-based solutions. However, such dispersions inherently peel upon application to the skin, rendering the dispersion unstable on its own. By the term unstable, it is meant that the composition peels or flakes upon application to the skin. Specifically, the dispersion flakes off the skin when applied, which makes the dispersion aesthetically and effectively unappealing for consumers requiring a skin care composition that provides lasting cosmetic benefits.

These dispersions have previously been used in personal care compositions; however, the amount utilized in previously disclosed compositions has been said to limit the silicone elastomer to no more than 30% by weight of the composition, because stability of water-based compositions may be compromised by higher quantities (U.S. Pat. No. 5,871,761). Applicants have observed that in these high quantities, the composition is considered unstable, whereby upon application of the composition on the skin, peeling and flaking of the composition on the skin is observed, as shown in Table 2 below. However, it was also observed that a substantial enhancement of the inherent properties of the water-based composition is achieved with the higher amounts of aqueously dispersed silicone elastomer used in the composition. In particular, it was unexpectedly observed that compositions containing greater than 30% of aqueously dispersed elastomer not only smooth and mattify the look of skin, but also mask the appearance of lines and wrinkles. Thus, there is substantial motivation to use larger quantities of the aqueously dispersed elastomer, if the flaking/instability issue could be solved.

In the present invention, it has been surprisingly found that combining a specific emollient system with the aqueous dispersion of silicone elastomers can stabilize the composition even with a relatively high amount of the silicone elastomer present in the final composition. Moreover, such a combination, when topically applied, surprisingly and rapidly reduces the appearance of lines and wrinkles on human skin, as can be seen in the Examples provided herein below.

As a first essential element, an aqueous dispersion of silicone elastomer is used in the present inventive composition. The aqueous dispersion comprises an aqueous dispersion of cured silicone rubber particles. Such a dispersion is prepared by the in situ crosslinking reaction taking place in fine droplets of a liquid organopolysiloxane precursor for a silicone rubber emulsified in an aqueous medium containing a surfactant. The method of crosslinking can be achieved by methods commonly known to those skilled in the art, but a preferred method is described in U.S. Pat. No. 5,871,761, which is incorporated by reference herein. In brief, a liquid precursor of a silicone rubber, which is a mixture or combination of an organopolysiloxane having at least two alkenyl groups bonded to the silicone atoms in a molecule and an organohydrogenpolysiloxane having at least two hydrogen atoms directly bonded to the silicone atoms in a molecule, is first emulsified in an aqueous medium containing a surfactant as an emulsifier under agitation to form an aqueous emulsion, to which a catalytic amount of a platinum compound is added to catalyze the hydrosilation reaction which converts the droplets of liquid silicone rubber precursor into particles of a cured silicone rubber.

The alkenyl groups in the above mentioned alkenyl-containing organopolysiloxane can be vinyl groups or allyl groups, of which vinyl groups are preferred. The organic groups bonded to the silicone atoms in the alkenyl-containing diorganopolysiloxane other than the alkenyl groups preferably monovalent hydrocarbon groups having 1 to 20 carbon atoms free from aliphatic unsaturation, optionally, substituted for all or a part of the hydrogen atoms in the hydrocarbon groups by halogen atoms. The organopolysiloxane should have at least two of the alkenyl groups in a molecule in order for the liquid silicone rubber precursor to be converted into a cured silicone rubber.

Examples of the unsubstituted or halogen-substituted monovalent hydrocarbon groups free from aliphatic unsaturation include: alkyl groups such as methyl, ethyl, propyl, butyl, pentyl, hexyl, heptyl, octyl, nonyl, decyl, dodecyl, tetradecyl, hexadecyl and octadecyl groups; aryl groups such as phenyl and tolyl groups; aralkyl groups such as 2-phenylethyl and 2-phenylpropyl groups; and halogen-substituted alkyl groups such as 3,3,3-trifluoropropyl, 2-(perfluoro-n-butyl) ethyl and 2-(perfluoro-n-octyl) ethyl groups. Although the monovalent hydrocarbon groups of a single kind or two or more kinds in combination can be present in the alkenyl-containing organopolysiloxane, it is preferable that all or at least 90% by moles of the monovalent hydrocarbon groups other than alkenyl groups are methyl groups, the balance, if any, being phenyl groups.

The organohydrogenpolysiloxane to be combined with the above described alkenyl-containing organopolysiloxane to form a liquid silicone rubber precursor should have at least two hydrogen atoms directly bonded to the silicone atoms in a molecule. The organic groups bonded to the silicone atoms in the organohydrogen polysiloxane molecules can be selected from the unsubstituted or halogen-substituted monovalent hydrocarbon groups free from aliphatic unsaturation as exemplified above relative to the alkenyl-containing organopolysiloxane. It is also preferable that all or at least 90% by moles of the monovalent hydrocarbon groups free from aliphatic unsaturation are methyl groups, the balance, if any, being phenyl groups. The blending proportion of the alkenyl group-containing diorganopolysiloxane and the organohydrogenpolysiloxane is such that the molar ratio of the alkenyl groups in the alkenyl group-containing diorganopolysiloxane to the silicone-bonded hydrogen atoms in the organohydrogenpolysiloxane is in the range from 0.8 to 1.2.

The crosslinking density in the cured silicone rubber particles is determined by the contents of the alkenyl groups in the alkenyl-containing organopolysiloxane and the silicone-bonded hydrogen atoms in the organohydrogenpolysiloxane, which must be appropriately selected so that the silicone rubber particles formed by the in situ crosslinking reaction may have a rubber hardness in the JIS A scale in the range from 10 to 90 or, preferably, from 20 to 80 as measured according to the procedure specified in JIS K 6301.

It is a desirable condition that the configuration of the globular silicone rubber particles in the aqueous dispersion is as close to spherical as possible with an aspect ratio, i.e. the ratio of the longer axis to the shorter axis, not exceeding 1.2 or, more desirably, not exceeding 1.1.

The cured silicone rubber particles are silicone elastomers. The average particle size of the cured silicone rubber particles is in the range of from 0.1 to 100 μm or, preferably, from 1 to 10 μm. In the preferred embodiment, the aqueous dispersion contains dimethicone/vinyldimethicone crosspolymers as the cured silicone rubber particles. In the preferred embodiment, more than 30%, preferably at least about 40%, more preferably at least about 60% by weight of the composition, of aqueously dispersed cured silicone rubber is used.

As noted above, the aqueous dispersion of silicone elastomers contains at least one surfactant used in the preparation of the aqueous emulsion of the organohydrogenpolysiloxane. The surfactant may be nonionic, anionic, cationic, or amphoteric in nature, as long as the surfactant is compatible with the surfactant contained in the base mixture of the skin-care water-base composition to which the aqueous dispersion of the silicone elastomer is to be added.

Examples of the nonionic surfactant include polyoxyethylene alkylphenyl ethers, polyoxyethylene alkyl ethers, polyoxyethylene sorbitan fatty esters, glycerine fatty acid esters and the like having an HLB value in the range from 1.5 to 20, preferably from 7 to 19. Examples of anionic surfactants include salts of alkyl sulfates, salts of alkylbenzene sulfonates, salts of dialkyl sulfosuccinates, salts of alkyl phosphoric acids, salts of polyoxyethylene alkyl ether sulfates, polyoxyethylene alkylphenyl ether sulfates and the like. Examples of cationic surfactants include long-chain alkyl trimethyl ammonium chlorides, alkylamine hydrochlorides, alkylamine acetates, long-chain alkyl phenyl dimethyl ammonium chlorides and the like. Examples of the amphoteric surfactants include N-acylamidopropyl-N, N-dimethylammonio beatines, N-acylamidopropyl-N,N'-dimethyl-N'-2-hyroxypropylammonio betaines and the like.

The amount of surfactant is determinative of the particle size distribution of the siloxane droplets and therefore the average particle diameter of the cured silicone rubber particles. Therefore, the amount of surfactant should be selected depending on the desired average particle size of the silicone rubber particles. In the preferred embodiment, the surfactant is nonionic, preferably a polyoxyethylene alkyl ether, and is used in amount between 0.1% to 20% by weight of the composition, preferably from 0.2% to 20%, and most preferably from 10% to 20%. The preferred nonionic surfactant used is C12-C14 pareth-12.

The preferred aqueous dispersion of silicone elastomer in the present invention is dimethicone/vinyldimethicone crosspolymer/C12-C14 Pareth-12/Water, and is available in commercial form from Shin-Etsu Chemical Co., Ltd under the commercial name DC 9509 Silicone Elastomer Suspension.

The second essential element of the present invention is an emollient system. As discussed hereinabove, the aqueously dispersed silicone elastomers are normally unstable in high concentrations in a water-base composition, as shown in Example 4 discussed below. It has been surprisingly discovered that addition of specific emollients with the aqueous dispersion of silicone elastomers, provides stability to the composition when the aqueously dispersed silicone elastomer is used in relatively high amounts. The emollients used are solid and have a melting point close to or at skin temperature, which is about 37° C. While not wishing to be bound by any theories, it is believed that such emollients act as a type of film former to enable a user to spread the inventive composition containing the aqueous dispersion of silicone elastomers onto the skin, while avoiding peeling or flaking upon application. Moreover, such emollients keep the elastomers on the skin after water evaporates. Emollients that are silicone-based would not be compatible, as is shown in Table 3 below.

The emollient system of the present invention contains at least one emollient selected from the list consisting of petrolatum, cocoa butter, beeswax and shea butter. The emollients may each be used alone or in any combination as long as the total in the composition is between 1 to 20%, preferably from 2% to 10% and most preferably from 3% to 7% by weight of the total composition. The preferred emollient system has a combination of shea butter, cocoa butter and beeswax.

The present inventive composition optionally comprises a film forming agent selected to further aid in uniformly distributing the composition upon the skin. Any film forming agent that is water-dispersible may be used. In the preferred embodiment, the film forming agent is selected from the group consisting of Glyceryl Oleate/Propylene Glycol, HDI/Trimethylol Hexyllacetone Crosspolymer/Silica, Sorbitan Sesquioleate, Polyglycerol-3 Diisotearate, Steareth-2, Polysorbate 40, Sorbitan Trioleate, Dimethicone//Dimethicone PEG-10/15 Crosspolymer, Isododecane//PEG-15/Lauryl Dimethicone Crosspolymer, PEG-11 Methyl Ether Dimethicone, Polyglyceryl-3 Disiloxane Dimethicone, and PEG-10 Dimethicone.

The preferred film forming agent in the present invention is HDI/Trimethylol Hexyllacetone Crosspolymer/Silica and is present in an amount from 0.01% to 20%, preferably from 1% to 15%, and most preferably from 5% to 10% by weight of the composition.

The preferred composition is in the form of an emulsion. In the preferred embodiment, the present invention is in the form of an oil-in-water emulsion, although it is contemplated that the present invention may also be in the form of a water-in-oil or water-in-silicone type emulsion. In the preferred embodiment, the water phase is present in an amount of from 30% to 55%.

The following examples further illustrate the novel compositions and methods of the present invention, but the invention is not limited thereto.

Example 1

The following composition provides an example of a preferred embodiment incorporating the inventive composition in the form of an emulsion. The examples that follow are conducted utilizing the composition below.

Composition

| Trade Name | CTFA name | Percent |
| --- | --- | --- |
| Deionized Water | Purified Water | 14.402500 |
| Glycerine USP 99% (Vegetable) | Glycerin | 0.500000 |
| Tristat SDHA | Sodium Dehydroacetate | 0.100000 |
| Shea Butter-Ultra Refined | Shea Butter (Butyrospermum Parkii) | 2.432500 |
| Cocoa Butter USP | Cocoa Butter | 2.432500 |
| Lanette O | Cetearyl Alcohol | 0.750000 |
| CS Lipid Complex | Propylene Glycol Dicaprylate/Cucumis Melo (Melon) Fruit Extract/Persea Gratissima (Avacado) Oil/Cholesterol/Potassium Sulfate | 0.200000 |
| NAB Cholesterol | Cholesterol | 0.200000 |
| Apigenin | Chamomilla Recutita (Matricaria) Extract | 0.050000 |
| Phytocohesine | Sodium Beta-Sitosterol Sulfate | 0.200000 |
| Biosine | Phytosphingosine/Propylene Glycol Dicaprate | 0.200000 |
| Beeswax-White S.P. 422P | Beeswax | 0.300000 |
| Patlac IL | Isostearyl Lactate | 0.973000 |
| Pationic ISL | Sodium Isostearoyl Lactylate | 0.486500 |
| DC 9509 Silicone Elastomer Suspension | Dimethicone/Vinyldimethicone Crosspolymer(63%)/C12–14 Pareth-12(3%)/Water(33%) | 60.00000 |
| DL Panthenol | Panthenol | 0.486500 |
| Antiglyskin | Water/Helianthus Annuus (Sunflower) Seed Extract | 0.486500 |
| Sensiva SC 50 | Ethylhexylglycerin | 0.500000 |
| Argireline Solution | Water (Aqua Purificata) Purified/Acetyl Hexapeptide-3 | 0.100000 |
| Diocide | Caprylyl Glycol/Phenoxyethanol/Hexylene Glycol | 1.000000 |
| Deliner AELA943S | Water (Aqua Purificata) Purified//Butylene Glycol/*Zea Mays* (Corn) Kernal Extract | 0.500000 |
| Biopeptide EL | Glyceryl Polymethacrylate/PEG-8/Palmitoyl Oligopeptide | 0.200000 |
| Siegesbeckia | Glycerin/Water/Siegesbeckia Orientalis Extract | 0.500000 |
| Deionized Water | Purified Water | 0.500000 |
| K3 Vita-C | Aminopropyl Ascorbyl Phosphate | 0.050000 |
| BPD-500 | HDI/Trimethylol Hexyllacetone Crosspolymer/Silica | 10.00000 |
| Timiron Silk Blue No. 17241 | Timiron Silk Blue No. 17241 Mica (77019), Titanium Dioxide (77891) | 0.350000 |
| Viscolam AT 64/P | Sodium Acrylate/Sodium Acryloydimethyl Taurate Copolymer/Hydrogenated Polydecene/Laureth-8 | 1.000000 |
| Silicone HL88 | Dimethicone | 1.000000 |

Example 2

The following clinical study is conducted using the composition of the present invention, presented hereinabove. The effects of application of the inventive composition on the skin of women is tested.

Formation of Study Panel:

Adult women who are interested in taking part in this study are recruited from a local population. The following criteria for inclusion and exclusion are based on the information obtained from the candidates and from an examination of the face and hands that are involved in the study.

Inclusion Criteria: To be Considered as a Potential Subject, Each Candidate Must:

have moderate to deep lines above the lips;
express willingness to cooperate with the investigator; and
demonstrates the ability to understand the purpose of the study and what is required of her to bring it to a meaningful conclusion.

Exclusion Criteria: A Prospective Participant is Excluded if the Interview or Examination Disclosed Any of the Following:

a systemic illness that contra-indicated participation;
any dermatological disorders in the areas that were to used in the study;
pregnant women or lactating mothers;
use of systemic or topical retinoids, antihistamines or similar agents.

Composition of Panel:

The panel is composed of 24 women who satisfy all the requirements itemized in the list of inclusion and exclusion criteria.

Method of Application:

The women are instructed to apply the product to the area above the lips two times daily, morning and evening. On the day of testing, the women do not apply the product for at least 12 hours before measurements are taken. Product use is monitored by a daily diary as well as assessment of remaining package content at the end of the study.

Clinical Test Procedure:

This is a controlled study which consists of two months product use. The test site is above the lips. The women refrain from using any treatment products on the test site except for the test product provided. Skin evaluations are carried out before treatment (baseline), and one, four and eight weeks during the course of treatment.

Skin Firmness

Skin firmness is assessed with the Ballistometer above the lips. The Ballistometer is an instrument that assesses the dynamic properties of the skin through the measurement of the rebound of a hard object on the surface of the skin. It measures skin elasticity by dropping a very light weight (1-5 grams) pendulum on the skin surface and measuring the rebound pattern of the pendulum via a computer. Once the probe hits the surface of the skin, the kinetic energy of the falling object is stored inside the skin, and is subsequently released to make the probe rebound at a smaller height than the initial starting position. To characterize the interaction between the pendulum and the skin, the differences in the amplitude of the first rebound are analyzed.

Skin Lifting

Skin lifting is measured with a Dermascan C® ultrasonic instrument (Cortex Technology, Hadsund, Denmark). A pulsed 20 MHz emission in B-mode is selected to give cross-sectional images of the skin in two dimensions. A template and 1 mm gel layer are used to ensure reproducibility of the images from visit to visit. Two images are taken from above the lips at each visit. A built-in image analysis program calculates the density of the dermis.

Lines & Wrinkles

Reduction of lines & wrinkles is assessed and documented with close up photography. Photos of the area above the lips are taken with a Fuji S2 digital camera. Panelists heads are placed in a head rest to insure reproducibility of positioning. The camera is positioned at a ratio of 1:3 at an F stop of 32. Photos are evaluated via an image analysis program, Optimas 6.51, comparing before and after product use. Fine lines and wrinkles are assessed by examining changes in the Integrated Optical Density (IOD) before and after product use. A decrease in IOD represents a decrease in fine lines and wrinkles and vise-versa.

Results:

TABLE 1

| | Percent Improvement | | |
|---|---|---|---|
| | 1 week | 4 weeks | 8 weeks |
| Firmness | 13% | 21% | 27% |
| Lifting | 19% | 35% | 45% |
| Lines & Wrinkles | 20% | 38% | 41% |

As shown in Table 1 above, the present inventive composition improved skin firmness, skin lifting, and the appearance of lines and wrinkles after 1, 4 and 8 weeks of product use. Specifically, the test results show that the composition of the present invention improves skin firmness by an average of 27%, improves skin lifting by an average of 45% and reduces the appearance of lines and wrinkles by an average of 41% after 8 weeks of product use as compared to pre-treatment.

Example 3

The following example provides the results, in Table 2 of the stability of different amounts of the dispersed silicone elastomer in the commercial composition. As can be seen below, the composition is unstable when the dispersed silicone elastomer reaches a concentration of 30%.

TABLE 2

| Sample # | Dispersed Silicone Elastomer % | Dispersed Silicone Elastomer (grams) | Commercial Composition in grams | COMMENTS |
|---|---|---|---|---|
| 1 | 5% | 2.5 | 47.5 | Stable |
| 2 | 10% | 5 | 45 | stable |
| 3 | 30% | 15 | 35 | not stable - peels a little |
| 4 | 50% | 25 | 25 | not stable - peels |
| 5 | 80% | 40 | 10 | not stable - peels |
| 6 | 90% | 45 | 5 | not stable - peels |

Example 4

The tables below show the inventive composition with different emollient systems. Table 3 shows the results of the inventive composition without any butters. As can be seen below, the inventive composition, in the absence of butters as emollients, is not stable at 40% of the dispersed silicone elastomer and above. Table 4 shows the inventive composition with methyl trimethicone as an emollient. As can be seen below, the inventive composition with methyl trimethicone as an emollient is not stable at 40% of the dispersed silicone elastomer and above. Table 5 shows the inventive composition with coco-caprylate/caprate as an emollient. As can be seen below, the inventive composition with coco-caprylate/caprate as an emollient is not stable at 40% of the dispersed silicone elastomer and above. Table 6 shows the inventive composition with the inventive emollient system, consisting of a class of butters and waxes. As can be seen below, the inventive composition with the inventive emollient system is stable until 80% of the dispersed silicone elastomer.

TABLE 3

Inventive Composition without butters

| Sample # | Inventive Composition % | Dispersed Silicone Elastomer % | Comments |
| --- | --- | --- | --- |
| 1 | 80 | 20 | Stable |
| 2 | 60 | 40 | not stable - peels a little |
| 3 | 40 | 60 | not stable - peels |
| 4 | 20 | 80 | not stable - peels |

TABLE 4

Inventive Composition with Methyl Trimethicone

| Sample # | Inventive Composition % | Dispersed Silicone Elastomer % | Comments |
| --- | --- | --- | --- |
| 1 | 80 | 20 | stable |
| 2 | 60 | 40 | not stable - peels a little |
| 3 | 40 | 60 | not stable - peels a lot |
| 4 | 20 | 80 | not stable - peels a lot |

TABLE 5

Inventive Composition with COCO-CAPRYLATE/CAPRATE

| Sample # | Inventive Composition % | Dispersed Silicone Elastomer % | Comments |
| --- | --- | --- | --- |
| 1 | 80 | 20 | stable |
| 2 | 60 | 40 | not stable - peels a little |
| 3 | 40 | 60 | not stable - peels a lot |
| 4 | 20 | 80 | not stable - peels a lot |

TABLE 6

Inventive Composition with inventive emollient system

| Sample # | Inventive Composition with inventive emollient system % | Dispersed Silicone Elastomer % | Comments |
| --- | --- | --- | --- |
| 1 | 80 | 20 | stable |
| 2 | 60 | 40 | stable |
| 3 | 40 | 60 | stable |
| 4 | 20 | 80 | not Stable - peels a little |

What is claimed is:

1. A method of reducing the appearance of lines and wrinkles comprising applying to the skin a stable, aqueous based, anti-aging composition that does not flake or peel when applied to the skin, comprising: above 40% by weight of aqueously dispersed cured silicone elastomer particles; and an emollient system comprising a combination of cocoa butter, beeswax and shea butter.

2. The method of claim 1 wherein the aqueously dispersed silicone elastomer particles are present in an amount above 60% by weight.

3. The method of claim 2 wherein the aqueously dispersed silicone elastomer is dimethicone/vinyldimethicone crosspolymer/C 12-14 Pareth-12/Water.

4. The method of claim 1 wherein the anti-aging composition further comprises a film-forming agent, the film-forming agent being a water-dispersible elastomer.

5. The method of claim 4 wherein the film-forming agent is HDI/Trimethylol Hexyllacetone Crosspolymer/Silica.

6. A method of improving skin condition comprising applying to the skin a stable, aqueous based, anti-aging composition that does not flake or peel when applied to the skin, comprising: above 40% by weight of aqueously dispersed cured silicone elastomer particles; and an emollient system comprising a combination of cocoa butter, beeswax and shea butter.

7. The method of claim 6 wherein the aqueously dispersed silicone elastomer particles are present in an amount above 60% by weight.

8. The method of claim 7 wherein the aqueously dispersed silicone elastomer is dimethicone/vinyldimethicone crosspolymer/C 12-14 Pareth-12/Water.

9. The method of claim 6 wherein the anti-aging composition further comprises a film-forming agent, the film-forming agent being a water-dispersible elastomer.

10. The method of claim 9 wherein the film-forming agent is HDI/Trimethylol Hexyllacetone Crosspolymer/Silica.

* * * * *